(12) United States Patent
Sinofsky

(10) Patent No.: US 6,168,591 B1
(45) Date of Patent: Jan. 2, 2001

(54) GUIDE FOR PENETRATING PHOTOTHERAPY

(75) Inventor: Edward L. Sinofsky, Dennis, MA (US)

(73) Assignee: CardioFocus, Inc., Norton, MA (US)

( * ) Notice: Under 35 U.S.C. 154(b), the term of this patent shall be extended for 0 days.

(21) Appl. No.: 08/991,429

(22) Filed: Dec. 16, 1997

Related U.S. Application Data

(63) Continuation-in-part of application No. 08/827,631, filed on Apr. 10, 1997, now Pat. No. 5,908,415, which is a continuation of application No. 08/303,605, filed on Sep. 9, 1994, now abandoned.

(51) Int. Cl.$^7$ ...................................................... A61B 17/36
(52) U.S. Cl. .................................. 606/15; 606/16; 606/2; 606/7
(58) Field of Search ........................... 606/2, 7, 10, 13–17

(56) References Cited

U.S. PATENT DOCUMENTS

| | | | |
|---|---|---|---|
| 5,163,935 | * 11/1992 | Black et al. | 606/15 |
| 5,169,395 | 12/1992 | Narciso, Jr. | 606/7 |
| 5,196,005 | * 3/1993 | Doiron | 606/15 |
| 5,415,653 | * 5/1995 | Wardle et al. | 606/15 |
| 5,441,497 | * 8/1995 | Narciso | 606/15 |
| 5,456,681 | * 10/1995 | Hajjar | 606/15 |
| 5,514,128 | * 5/1996 | Hillsman et al. | 606/15 |
| 5,536,265 | * 7/1996 | Van Den Brugh et al. | 606/15 |
| 5,643,253 | * 7/1997 | Baxter | 606/7 |
| 5,695,482 | * 12/1997 | Kaldany | 606/15 |
| 5,700,260 | * 12/1997 | Cho et al. | 606/15 |
| 5,807,383 | * 9/1998 | Kolesa | 606/7 |
| 5,855,577 | * 1/1999 | Murphy-Chutorian et al. | 606/7 |

FOREIGN PATENT DOCUMENTS

| | | |
|---|---|---|
| WO 92/17243 | 10/1992 | (WO) . |
| WO 95/09574 | 4/1995 | (WO) . |

* cited by examiner

Primary Examiner—Robert L. Nasser
(74) Attorney, Agent, or Firm—Thomas J. Engellenner; Nutter, McClennen & Fish, LLP

(57) ABSTRACT

Phototherapeutic instruments are disclosed having a light transmitting optical fiber with a flexible portion that facilitates passage of the instrument through a tortuous lumen within a patient and an outer support sheath slidably mounted about the fiber. In one preferred embodiment, the instrument includes a rigid light-emitting tip. The support sheath is configured to protect the more delicate optical fiber and provide support for the flexible portion of the optical fiber during penetration of the light-emitting tip into a patient's tissue. During insertion of the instrument into a tortuous lumen, the optical fiber is covered by the support sheath, allowing the light-emitting tip to deflect with ease as it travels along the tortuous lumen. Upon arrival of the light-emitting tip at the site of the target tissue, the operator moves the distal end of the apparatus into selected proximity with the target tissue, and then pushes the fiber element forcing the light-emitting tip to penetrate the target tissue. The flexible portion of the fiber element fits snugly in the sheath so that when the operator pushes on the fiber element from a remote location, the sheath-fiber element configuration provides enough force on the distal end of the light-emitting tip to penetrate the target tissue.

17 Claims, 4 Drawing Sheets

GUIDE FOR PENETRATING PHOTOTHERAPY

REFERENCE TO RELATED APPLICATIONS

This application is a continuation-in-part of U.S. patent application Ser. No. 08/827,631, incorporated herein by reference and filed Apr. 10, 1997, now U.S. Pat. No. 5,908,415, which is a file-wrapper continuation of U.S. patent application Ser. No. 08/303,605, incorporated herein by reference and filed Sep. 9, 1994, now abandoned.

GOVERNMENT RIGHTS

The U.S. Government has rights in this invention pursuant to National Institute of Health Grant No. 2 R44 HL 54397-02.

BACKGROUND OF THE INVENTION

The technical field of this invention is phototherapy and, in particular, instruments employing optical fibers or other flexible light waveguides to deliver radiation to a targeted biological site.

Fiber optic phototherapy is an increasingly popular modality for the diagnosis and/or treatment of a wide variety of diseases. For example, in surgery, infrared laser radiation will often be delivered to a surgical site via an optically transmissive fiber in order to coagulate blood vessels or cauterize tissue. Similar fiber optic delivery systems have been proposed for endoscopic or catheter-based instruments to deliver therapeutic radiation to a body lumen or cavity. U.S. Pat. No. 4,336,809 (Clark) and U.S. Reissue Pat. No. RE 34,544 (Spears) disclose that hematoporphyrin dyes and the like selectively accumulate in tumorous tissue and such accumulations can be detected by a characteristic fluorescence under irradiation with blue light. These patents further teach that cancerous tissue that has taken up the dye can be preferentially destroyed by radiation (typically by high intensity red light).

Others have proposed the use of fiber-delivered radiation to treat artherosclerotic disease. For example, U.S. Pat. No. 4,878,492 (Sinofsky et al.) discloses the use of infrared radiation to heat blood vessel walls during balloon angioplasty in order to fuse the endothelial lining of the blood vessel and seal the surface. Another application of fiber-delivered radiation is disclosed in U.S. Pat. No. 5,053,033 (Clarke) which teaches that restenosis following angioplasty can be inhibited by application of UV radiation to the angioplasty site to kill smooth muscle cells which would otherwise proliferate in response to angioplasty-induced injuries to blood vessel walls.

In yet another application, phototherapeutic instruments are employed to treat electrical arrhythmia of the heart. In such applications, a catheter having a fiber optic component is fed via a major artery into a patient's heart. Once inside the heart, a catheter senses electrical impulses with electrical contacts on its outer sheath or other catheter elements in order to locate the source of arrhythmia. Once located, the phototherapeutic component is activated to "ablate" a portion of the inner heart wall. The likelihood that the patient's heart will continue to experience arrhythmia is reduced by coagulating heart tissue in the vicinity of the arrhythmia source.

In other applications, laser radiation can be used in conjunction with a similar catheter instrument inside a patient's heart to increase blood flow to oxygen starved regions of the heart muscle. In such procedures, the laser radiation is used to form small holes in the heart muscle so that the oxygen-depleted tissue is bathed with blood from the ventricular cavity.

In all of these applications, if the light-emitting catheter instrument is too rigid, there is the potential for damage to a patient's artery or other blood vessel, especially the aorta. Furthermore, a rigid catheter instrument is difficult to steer to a desired location.

Accordingly, there exists a need for better apparatus for fiber-optic phototherapy. In particular, a phototherapeutic instrument that can "guide" an optical fiber with a light-emitting tip along a torturous lumen to the location of target tissue and then can penetrate the target tissue with the light-emitting tip would meet a particularly important need in the field of minimally-invasive phototherapeutic surgery.

SUMMARY OF THE INVENTION

Phototherapeutic instruments are disclosed having a light transmitting optical fiber with a flexible portion which facilitates passage of the instrument through a tortuous lumen within a patient, and an outer support sheath slidably disposed around the optical fiber. In one preferred embodiment, the instrument can further include a rigid light-emitting tip. The support sheath is configured to protect the more delicate optical fiber and provide support for the flexible portion of the optical fiber during penetration of the light-emitting tip into a patient's tissue. During insertion of the instrument into a tortuous lumen, the distal end of the optical fiber is covered by the support sheath. In a preferred embodiment the tip of the sheath articulates, i.e., the tip is steerable. The flexible portion of the fiber and the steerable tip of the sheath allow the distal end of the optical fiber-sheath apparatus to deflect as it travels along a tortuous lumen. When the fiber is retracted in the support sheath, the flexible region coincides with the articulated region of the steerable catheter.

When the distal end or tip of the optical fiber arrives at the site of the target tissue, the tip is advanced to the target tissue region (e.g., the heart wall). While the sheath is held still, the fiber element carried within the sheath is then mechanically advanced by itself, forcing the light-emitting tip to penetrate the target tissue. The flexible portion of the fiber element fits snugly in the sheath so that when an operator pushes on the fiber element from a remote location, the sheath-fiber element configuration transmits enough force on the proximal end of the light-emitting tip to advance the tip to penetrate the target tissue. Preferably, the clearance between the flexible portion of the fiber element and the rigid sheath is about 100 micrometers to about 500 micrometers.

A phototherapeutic instrument according to one embodiment of the invention includes a light transmitting optical fiber, and a support sheath slidably mounted about the fiber. The fiber has a proximal and a distal end. The proximal end is adapted for coupling to a source of phototherapeutic radiation. The distal end has an element for directing radiation into biological tissue. The fiber includes a first, stiff portion, a second, flexible portion connected to the distal end of the first stiff portion, and a third, stiff portion connected to the distal end of the second, flexible portion and forming the distal end of the fiber. Thus, the fiber's distal end can be covered by the support sheath as the fiber's distal end is advanced to a target site and then once the fiber's distal end has been positioned at the target site, a selected portion of the fiber's distal end can be extended outside the support sheath for insertion into the tissue. In other words, a phototherapeutic instrument according to one embodiment of the invention is configured to provide the instrument with gradient stiffness or a gradient flex property, e.g., an instrument with a sequence of stiff-floppy-stiff portions.

The invention is particularly useful in assisting an optically-transmissive fiber element's insertion along a tortuous lumen and in facilitating the penetration of the light-emitting tip of the fiber element into target tissue, thereby, reducing the possibility of fiber damage and/or perforation of a body lumen or organ. The invention is useful in placing an ablative laser radiation device into the ventricle of the heart when performing arrhythmia-correcting laser ablative procedures or when revascularizing the heart percutaneously. In these types of procedures, the surgeon seeks to pass the phototherapeutic instrument over the aortic arch and to partially penetrate the heart muscle. The instrument configurations of the present invention allow passage of a light-emitting tip of a phototherapeutic through a torturous lumen while providing stability to the fiber element during insertion and operation of the light-emitting tip of the fiber element.

The invention will next be described in connection with certain preferred embodiments. However, it should be clear that various changes and modifications can be made by those skilled in the art without departing from the spirit or scope of the invention.

DETAILED DESCRIPTION

Figure 1:
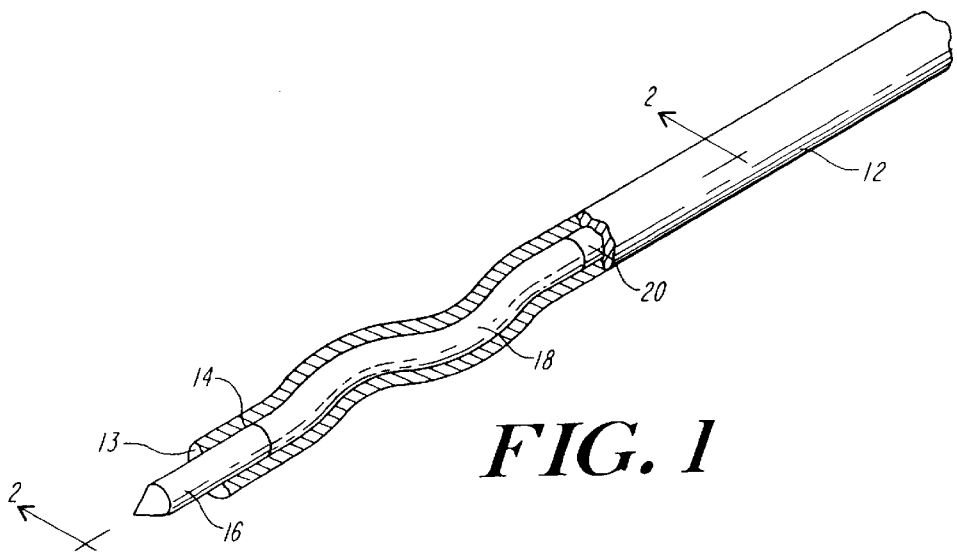
FIG. 1 a schematic, perspective field of view of the distal end of a phototherapeutic apparatus in accordance with the present invention.

In FIG. 1, one embodiment of a phototherapeutic apparatus 10 is illustrated having a tubular sheath 12 and an inner optically-transmissive fiber element 14. The optically-transmissive fiber element 14 includes a light-transmitting optical fiber 20, a flexible portion 18 which facilitates passage through a tortuous lumen within a patient, and a rigid light-emitting tip 16. The outer sheath 12 is configured to protect the more delicate fiber element 14 and provide support for the flexible portion 18 of the fiber element 14 during penetration of the light-emitting tip 16 into a patient's tissue.

During passage of the instrument 10 along a tortuous lumen, the fiber element 14 is covered by the support sheath 12, allowing the apparatus including the light-emitting tip 16 and sheath 12, i.e., the combined fiber-sheath system, to deflect with ease as it travels along the tortuous lumen and allowing the sheath 12 to guide the fiber element 14.

Figure 2:
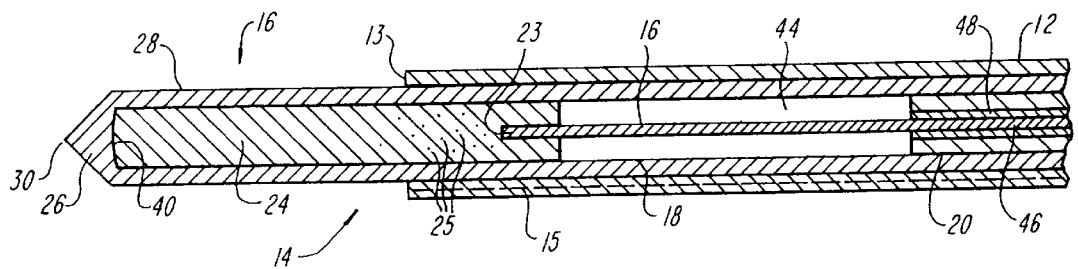
FIG. 2 is a cross-sectional view along the longitudinal axis of the phototherapeutic apparatus of FIG. 1.

FIG. 2 is a more detailed cross-sectional view of the distal end of the apparatus of FIG. 1. The optically-transmissive element is shown having an optical fiber 20 and a flexible portion 18. The optical fiber 20 has an optically transmissive core 46 surrounded by a cladding, and buffer coating. The flexible portion 18 also contains the optically transmissive core 46. The end face 23 of the core 46 is inserted into a housing 28 which makes up the outer surface of the rigid light-emitting tip 16.

The rigid light-emitting tip can include a diffuser assembly. The diffuser assembly can include a scattering medium 24 with optional individual scattering particles 25. Preferably, the medium 24 has a greater refractive index than the housing 28. At the distal end of the housing 28, an end cap 26 can be disposed. Optionally, the end cap may also be fitted with a reflective mirror 40. The end cap can further be ground or polished to a point 30 to facilitate penetration of body tissue.

Light propagating through the optical fiber core 22 is transmitted through the flexible portion 18 into the scattering medium and scattered in a cylindrical pattern along the length of the assembly 16. Each time the light encounters a scattering particle, it is deflected and, at some point, the net deflection exceeds the critical angle for internal reflection at the interface between the housing 28 and the medium 24. When this happens the light will exit. The housing can either be made sufficiently long to ensure that virtually all of the light entering it is eventually scattered and diffused in a single path, or as noted above, a reflective mirror can be fitted to the distal end of each diffuser assembly.

When a mirror is employed, light propagating through the medium 24 will be at least partially scattered before it reaches mirror 40. Light which does not exit during this initial pass through the tip will be reflected by mirror 40 and returned through the tip assembly. During the second pass, the remaining radiation (or at least a major portion of this returning radiation) again encounters the scattering particles which provide further radial diffusion of the light.

Thus, according to the embodiment illustrated in FIGS. 1 and 2, a phototherapeutic apparatus according to the invention includes a light transmitting optical fiber 14, and a support sheath 12 slidably mounted about the fiber. The sheath 12 can include a steering assembly, such as a wire 15. When pulled the tension on the wire 15 deflects the distal end of the phototherapeutic apparatus. Thus, by pulling on the wire 15 an operator can steer the apparatus along a tortuous lumen. The fiber 14 has a proximal and a distal end. The proximal end is adapted for coupling to a source of phototherapeutic radiation 36. The distal end has an element 16 for directing radiation into biological tissue. The fiber includes a first, stiff portion 20, a second, flexible portion 18 connected to the distal end of the first stiff portion 20, and a third, stiff portion 16 connected to the distal end of the second, flexible portion 18 and forming the distal end of the fiber 14. Thus, the fiber's distal end can be covered by the support sheath 12 as the fiber's distal end is advanced to a target site and then once the fiber's distal end has been positioned at the target site, a selected portion of the fiber's distal end can be extended outside the support sheath 12 for insertion into tissue. In other words, a phototherapeutic instrument according to one embodiment of the invention is configured to provide the instrument with gradient stiffness or a gradient flex property, e.g., an instrument with a sequence of stiff-floppy-stiff portions.

Figure 6A:
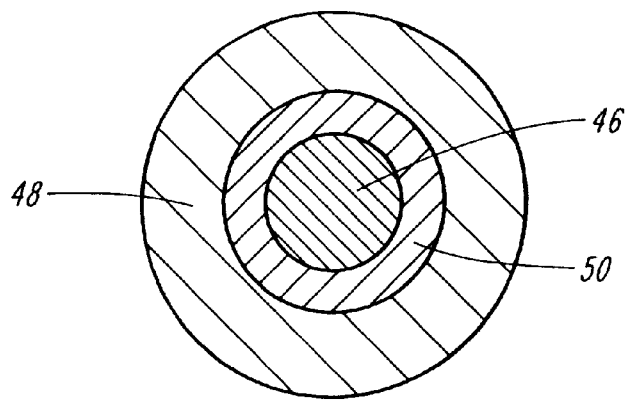
FIG. 6A is a cross-sectional view of the first, stiff portion of the optical fiber of FIG. 1.
Figure 6B:
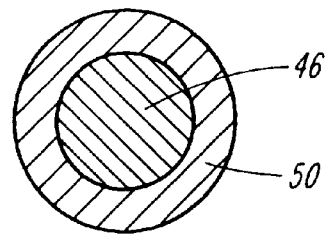
FIG. 6B is a cross-sectional view of the second, flexible portion of the optical fiber of FIG. 1.
Figure 6C:
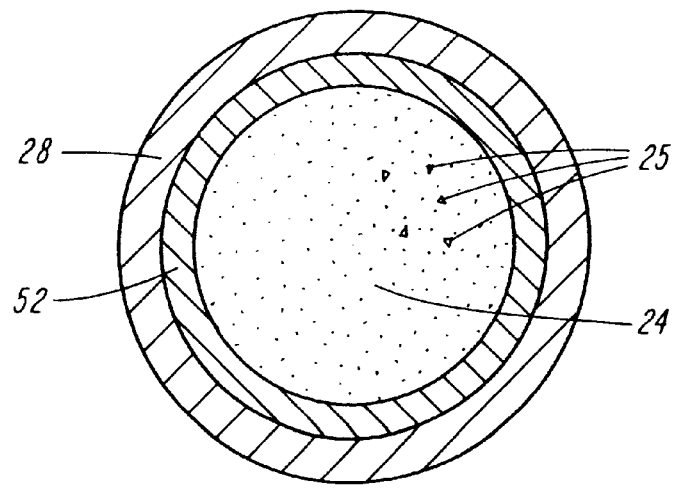
FIG. 6C is a cross-sectional view of an alternative embodiment of the third, stiff portion, i.e., the distal end or rigid light-emitting tip, of the optical fiber of FIG. 1.

The first, stiff portion 20, as shown in FIG. 6A, includes a glass fiber 46 for transmitting the radiation from the radiation source 36 to the light-emitting tip 16 of the fiber 14. The first, stiff portion 20 also includes lexan tubing 48. The first stiff portion 20 can also include buffer material surrounded by the lexan tubing 48. The lexan tubing 48 provides additional rigidity to the first, stiff portion 20. The second, flexible portion, as shown in FIG. 6B, includes the glass fiber 46 and a buffer material 50. In other words, the flexible region is a small buffered fiber. The third, stiff portion, i.e., the distal portion or light-emitting tip of the optical fiber, as shown in FIG. 2, can include a housing 28 filled with a scattering medium 24. Alternatively, the third stiff, portion, as shown in FIG. 6C, can include a scattering medium 24 surrounded by a glass tube 52, surrounded by a Teflon® coated capillary tubing 28.

The stiffness of some of the materials mentioned above was measured by applying a force on a fiber or tube of the material 15 mm from a point where the fiber/tube was supported and deflecting the fiber/tube 5 mm. For quartz tubing having an outer diameter of 450 microns and an inner diameter of 270 microns, about 9 g was required to deflect the fiber 5 mm. For Fiber/Lexan, i.e., 230 microns glass surrounded by a Teflon coating resulting in an outer diameter of 500 microns, about 9 g was required to deflect the structure 5 mm. About 5 g was required to deflect just a 230 micron diameter glass fiber 5 mm. Finally, about 6 g was required to deflect a lexan tube having an inner diameter of 500 microns and an outer diameter of 860 microns.

An exemplary manufacturing process suitable for joining a diffuser assembly to a glass-clad or polymer-clad optical fiber having a flexible portion and an outer diameter of about 50 to about 1000 micrometers can begin by stripping off the buffer from the end of the optical fiber, e.g., exposing about two or three millimeters of the inner fiber core and its cladding. It is not necessary to strip the cladding away from the core. Prior to stripping, the fiber end face preferably should be prepared and polished as known in the art to minimize boundary or interface losses. A transparent tubular structure which will form the housing for the scattering medium is then slipped over the prepared fiber end and, preferably slid beyond the fiber end. For example, if a manufacturer desires a tip assembly of about 20 millimeters, the tubing can be about 100 millimeters long and slid over about 80 millimeters of the fiber, leaving an empty lumen of about 20 millimeters in front of the fiber end face. In one preferred embodiment, the housing is Teflon® FEP tubing, available, for example, from Zeus Industries (Raritan, N.J.).

The assembly can then be injected with a scattering-loaded material, such as a silicone, epoxy or other polymeric material (if a solid diffuser is desired) or a suitable liquid, such as water or a deuterium oxide solution, containing colloidal scattering articles, such as silica, alumina, or titania, (if a liquid diffuser is desired). One exemplary scattering medium can be formulated by mixing 70 parts of clear silicone, Mastersil™ Formula 151-Clear (available from Masterbond, Inc. of Hackensack, N.J.) with one part of titania filled silicone, Mastersil™ Formula 151-White (also available from Masterbond), and a conventional silicone curing or hardening agent. The tube lumen should be completely filled with the silicone, epoxy or other carrier mixture to avoid entrapment of air bubbles.

The reflector (e.g., an aluminum, gold or other reflector-coated plug) is inserted into the distal end of the tube. The reflector at the distal end of the scattering tube can be a deposited metal or dielectric coating. In one preferred embodiment, a room temperature hardening agent is used and the diffuser assembly is simply allowed to solidify overnight.

It should be clear that the manufacturing processes described above are merely illustrative, and various alternative techniques can be practiced to construct the fiber tip assemblies of the present invention. For example, automated extrusion methods and/or injection molding approaches can be employed to mass produce fibers with integral diffusive tip assemblies.

Various other diffusive tip assemblies can be employed in the present invention. For a detailed discussion of various alternative embodiments see commonly-owned co-pending U.S. patent application Ser. No. 08/303,605 filed Sep. 9, 1994, entitled "PHOTOTHERAPY METHODS AND APPARATUS", by Edward L. Sinofsky, incorporated herein by reference.

Figure 3:
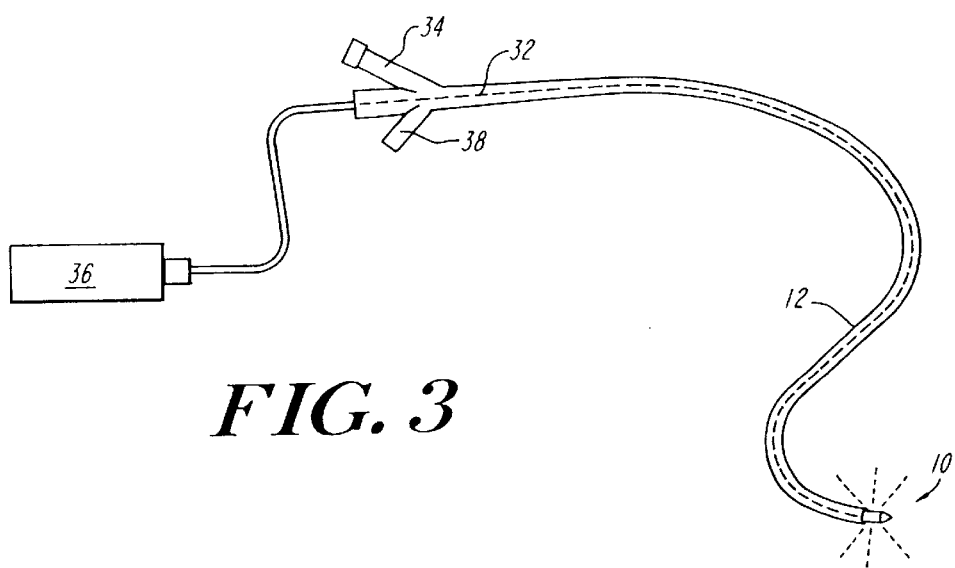
FIG. 3 is a schematic view of apparatus of FIG. 1 as part of a guiding catheter or endoscopic system.

In FIG. 3, one embodiment of the phototherapeutic apparatus according to the present invention 10 is shown schematically. The diffuser apparatus with its flexible portion and rigid light-emitting tip is coupled to a source of phototherapeutic radiation 36, (e.g., a laser). As shown in FIG. 3, the diffuser assembly can be designed to fit within a standard guiding catheter 32. The catheter 32 can further include electrical sensing elements 34 (e.g., dosimeters and the like) and/or at least one additional channel 38 for introduction of saline or therapeutic solutions.

Figure 4A:
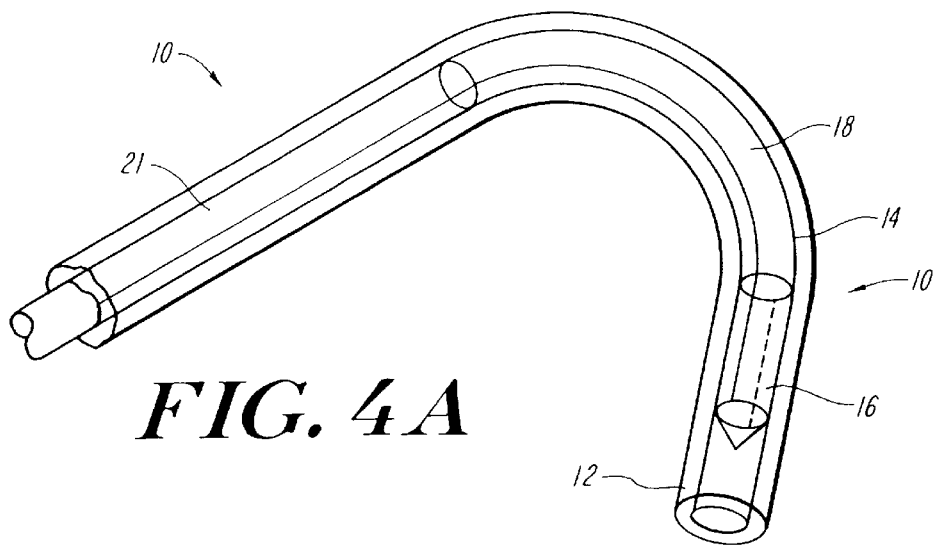
FIG. 4A illustrates the phototherapeutic apparatus of FIG. 1 in a deflected state.
Figure 4B:
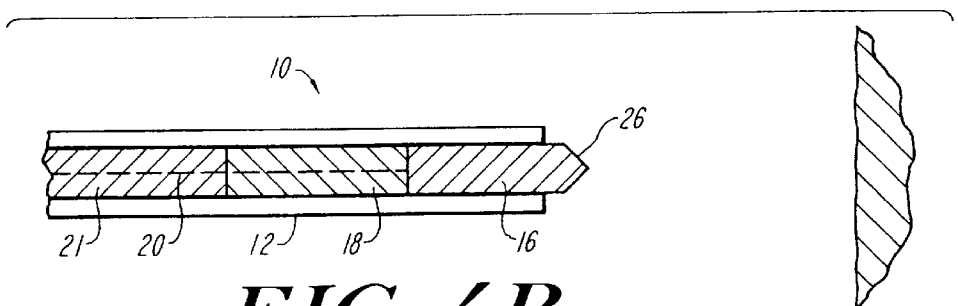
FIG. 4B illustrates the phototherapeutic apparatus of FIG. 1 deployed in an initial position prior to contacting the surface of a body organ or lumen.

Thus, as mentioned above, the instrument 10 can be inserted along a tortuous lumen. As the instrument passes along the tortuous lumen, the distal end of the instrument will deflect, as shown in FIG. 4A. The distal end of the fiber element 14 is covered by the sheath 12. The flexible portion 18 of the fiber element 14 allows the fiber element—sheath combination to deflect as it travels along a tortuous lumen. Upon successful passage along a tortuous lumen, the distal end of the instrument will arrive at a target site, as shown in FIG. 4B. As illustrated, the instrument 10 is positioned next to a segment of a patient's body tissue where penetration and radiation is desired. As shown, the apparatus includes an outer sheath 12 and an inner optically-transmissive fiber element 14. As described with reference to FIGS. 1 and 2, the fiber element 14 includes an optical fiber 20, a flexible portion 18 and a light-emitting tip 16. As stated above, during insertion of the instrument 10 into a tortuous lumen, the distal end of the fiber element 14 is covered by the support sheath 12, allowing the light-emitting tip 16 to deflect within the sheath 12 as it travels along the tortuous lumen. FIG. 4B, shows the fiber element 14 once it has been inserted along a tortuous lumen.

Figure 4C:
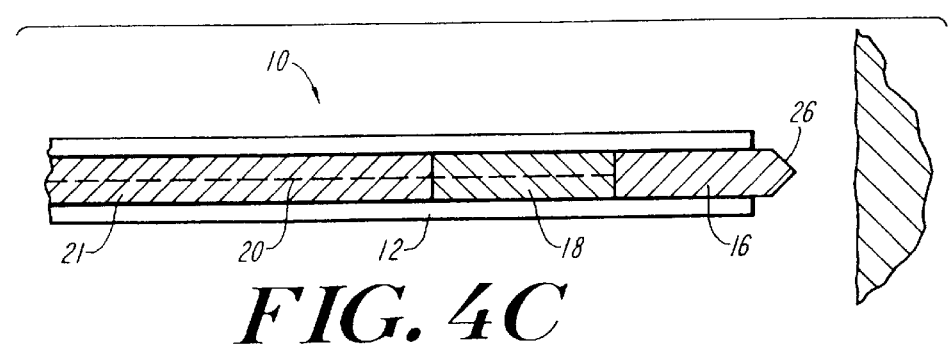
FIG. 4C is a further schematic illustration of the phototherapeutic apparatus of FIG. 4A after being moved into proximity with the target tissue.
Figure 4D:
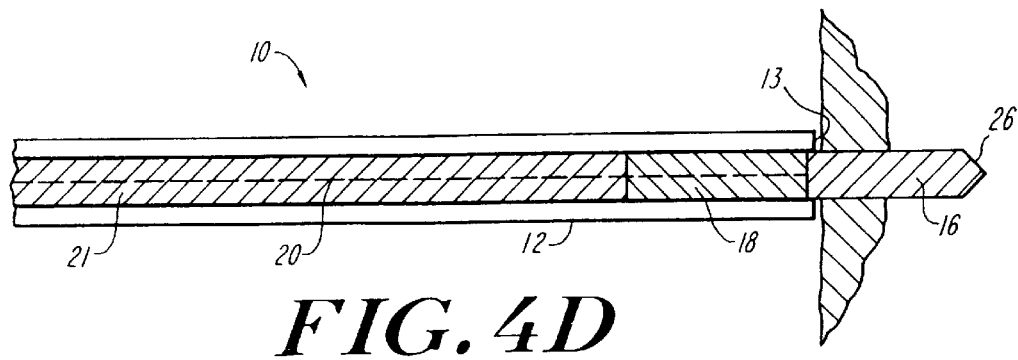
FIG. 4D is a further illustration of the apparatus of FIG. 4A after penetration of the target tissue by the light emitting tip.

Upon inserting the distal end of the fiber along a tortuous lumen, the distal end is positioned in proximity to the target tissue, as shown in FIG. 4C. Subsequent to positioning the distal end of the instrument close to the target tissue, the fiber element is pushed forward forcing the light-emitting tip to penetrate the tissue, as shown in FIG. 4D. The flexible portion of the fiber element fits snugly into the sheath so that when the fiber element is pushed forward from a remote location, the sheath-fiber element configuration transmits enough force on the distal end of the light-emitting tip to advance the tip to penetrate the target tissue. In this illustration, the optically-transmissive fiber has penetrated the patient's tissue but the distal end 13 of sheath 12 has not yet touched the tissue surface.

In one preferred embodiment, the fiber clement 14 and sheath 12 are constructed with sufficient clearance to permit saline or other therapeutic liquids to be released during the procedure. In particular, saline flushing of the light-emitting tip 16 may be desirable to cool the tissue surface proximal to the treatment site and to help limit the entry of blood into the apparatus, e.g., between the sheath 12 and the fiber element 14. However, the clearance between flexible portion 18 and the rigid sheath is minimal to avoid bunching of the flexible portion when the operator pushes on the fiber element. Preferably, the clearance between the flexible portion of the fiber element 14 and the rigid sheath 12 is about 100 micrometers to about 500 micrometers.

Various materials can be used to form the outer sheath including, for example, Teflon® and other fluorocarbon polymers. The struts can be formed by axial slices at various locations on the sheath. For example to construct a four strut stopper device, one would make four longitudinal cuts into the sheath, separated by 90° from each other. The length of the cuts will determine the radial extent of the stopper. In one embodiment it may also be desirable to fill the sheath polymer with a radio-opaque substance, such as barium in order to permit visualization under angiography.

Figure 5A:
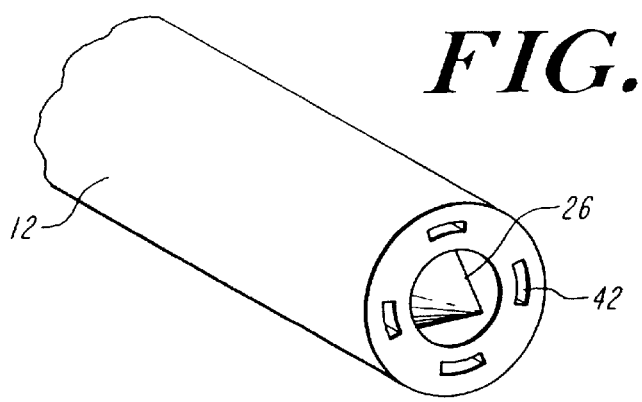
FIG. 5A is a perspective view of an alternative embodiment of a phototherapeutic apparatus according to the invention.
Figure 5B:
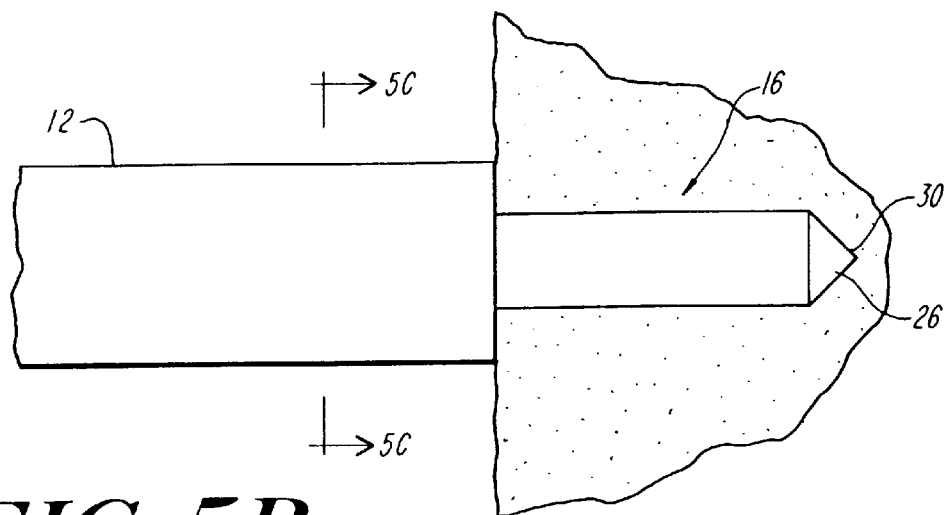
FIG. 5B is a cross-sectional view, along the longitudinal axis of the apparatus of FIG. 5A.
Figure 5C:
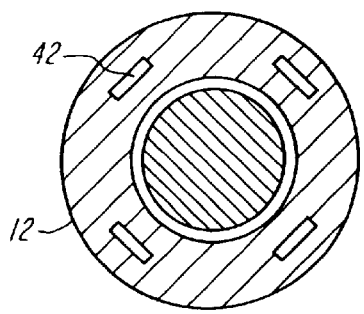
FIG. 5C is a cross-sectional view, along line C—C, of the apparatus of FIG. 5B.

With reference to FIGS. 5A–5C, another embodiment of a phototherapeutic apparatus according to the invention includes ports 42. The ports 42 can be suction ports for assisting in maintaining the sheath in contact with the target tissue or the ports 42 can be flushing ports for flushing the target tissue with therapeutic fluid.

Since certain changes can be made in the above constructions without departing from the scope of the invention, it is intended that all matter contained in the above description or shown in the accompanying drawings be interpreted as illustrative and not in a limiting sense.

Having described the invention, what is claimed as new and desired to be secured by Letters Patent is:

1. A phototherapeutic apparatus comprising
   a light transmitting fiber element having a proximal end and a distal end, the fiber element including a fiber core, the proximal end being adapted for coupling to a source of phototherapeutic radiation, the distal being adapted for penetrating tissue, the fiber element including
     a first portion including a relatively stiff tubular member, the first portion having a first stiffness;
     a second portion distal to the first portion, the second portion having a second stiffness less than the first stiffness; and
     a third portion distal to the second portion, the third portion having a third stiffness greater then the second stiffness, the third portion being adapted for emitting radiation from the fiber core to treat tissue; and
   a support sheath mounted about the fiber element such that the third portion of the fiber element is extendable from the support sheath by applying an axially compressive force to the fiber element, wherein the first, second and third stiffnesses of the fiber element provide a stiffness differential for facilitating passage of the fiber element through a tortuous lumen in a patient, and the support sheath minimizes flexing of the second portion of the fiber element as the third portion is extended from the support sheath.

2. The apparatus of claim 1 wherein the third portion of the fiber element comprises a diffuser assembly to diffuse radiation into said tissue.

3. The apparatus of claim 2 wherein the diffuser assembly comprises a light transmissive housing having a light scattering medium disposed therein.

4. The apparatus of claim 3 wherein the housing further includes an end cap having a reflective surface such that light radiation propagates through said fiber and enters the scattering medium and a portion of the radiation is emitted outward through said housing, and another portion is reflected by the reflective surface of the end cap for re-transmission through said scattering medium and further outward emission.

5. The apparatus of claim 3 wherein the scattering medium further comprises a medium having light-scattering particles dispersed therein.

6. The apparatus of claim 5 wherein the scattering particles are chosen from the group consisting of alumina, silica, titania compounds and mixtures thereof.

7. The apparatus of claim 3 wherein the housing is made of a polymeric material.

8. The apparatus of claim 7 wherein the polymeric material is a fluorocarbon polymer.

9. The apparatus of claim 2 wherein the diffusing tip assembly comprises a pointed tip element.

10. The apparatus of claim 1 wherein the fiber further comprises a rigid pointed tip connected to the distal end of the flexible portion.

11. The apparatus of claim 1 wherein the length of the second portion of the fiber element is between about 1 cm and about 4 cm.

12. A phototherapeutic apparatus comprising
   a light transmitting fiber element including a core and having a proximal end and a distal end,
   the proximal end adapted for coupling to a source of phototherapeutic radiation,
   the distal end adapted for directing the radiation into biological tissue,
   the fiber element including
     a first portion having proximal and distal ends and a first stiffness, the first portion including a relatively stiff tubular member,
     a second portion having proximal and distal ends, the proximal end being connected to the distal end of said first portion, the second portion having a second stiffness that is less than the first stiffness, and
     a third portion connected to the distal end of said second portion, the third portion having a third stiffness that is greater than the second stiffness, and
   a support sheath slidably mounted about the fiber element, such that the third portion of the fiber element is extendable from the support sheath by applying an axially compressive force to the fiber element, wherein the support sheath minimizes flexing of the second portion as the fiber element is extended from the support sheath.

13. The apparatus of claim 12 wherein said second portion of the fiber element comprises
   a flexible buffer material surrounding the core.

14. The apparatus of claim 12 wherein said first portion comprises
   a flexible, buffer material surrounding the core, and
   a relatively stiff tubular member surrounding the buffer material and extending along the longitudinal axis of the fiber to increase the rigidity of the first portion in relation to the second portion.

15. The apparatus of claim 12 wherein the clearance between the second portion of the fiber element and the support sheath is about 100 micrometers to about 500 micrometers.

16. The apparatus of claim 12 wherein the apparatus further comprises a delivery port to delivery a fluid in selected proximity to the distal end of the support sheath.

17. The apparatus of claim 12 wherein the third portion of the fiber element includes a diffuser assembly.

* * * * *

UNITED STATES PATENT AND TRADEMARK OFFICE
CERTIFICATE OF CORRECTION

PATENT NO. : 6,168,591 B1
DATED : January 2, 2001
INVENTOR(S) : Edward L. Sinofsky It is certified that error appears in the above-identified patent and that said Letters Patent is hereby corrected as shown below:

Col. 1, line 31: Reads: "U.S. Pat. No. 4, 336,809"

Should read: --U.S. Pat. No. 4,336,809--

Col. 5, line 56: Reads: "colloidal scattering articles,"

Should read: --colloidal scattering particles,--

Col. 6, line 62: Reads: "the fiber clement"

Should read: --the fiber element--

Signed and Sealed this

Twenty-ninth Day of May, 2001

Attest:

NICHOLAS P. GODICI

*Attesting Officer*   *Acting Director of the United States Patent and Trademark Office*